(12) United States Patent
Akaji

(10) Patent No.: US 9,019,365 B2
(45) Date of Patent: Apr. 28, 2015

(54) GOB INSPECTION SYSTEM FOR GLASS PRODUCT

(75) Inventor: Koichi Akaji, Kanagawa (JP)

(73) Assignee: Toyo Seikan Group Holdings, Ltd., Tokyo (JP)

( * ) Notice: Subject to any disclaimer, the term of this patent is extended or adjusted under 35 U.S.C. 154(b) by 225 days.

(21) Appl. No.: 13/823,399

(22) PCT Filed: Sep. 17, 2010

(86) PCT No.: PCT/JP2010/066217
§ 371 (c)(1),
(2), (4) Date: Mar. 14, 2013

(87) PCT Pub. No.: WO2012/035656
PCT Pub. Date: Mar. 22, 2012

(65) Prior Publication Data
US 2013/0176421 A1    Jul. 11, 2013

(51) Int. Cl.
*G01T 5/00* (2006.01)
*G06T 7/00* (2006.01)
*B07C 5/34* (2006.01)
*G01N 21/85* (2006.01)
*G01N 33/38* (2006.01)
*G01N 21/958* (2006.01)
*G01N 21/896* (2006.01)

(52) U.S. Cl.
CPC .............. *G06T 7/0004* (2013.01); *B07C 5/3408* (2013.01); *G01N 21/85* (2013.01); *G01N 21/958* (2013.01); *G01N 33/386* (2013.01); *G01N 21/896* (2013.01)

(58) Field of Classification Search
USPC ........................................................ 348/92
See application file for complete search history.

(56) References Cited

U.S. PATENT DOCUMENTS

2004/0194506 A1 * 10/2004 Ueda et al. .................... 65/29.11

FOREIGN PATENT DOCUMENTS

| JP | 63-52326 | 10/1988 |
|---|---|---|
| JP | 7-33445 | 2/1995 |
| JP | 7-103915 | 4/1995 |
| JP | 2000-19130 | 1/2000 |
| JP | 2003-4649 | 1/2003 |
| JP | 2003-262843 | 9/2003 |
| JP | 2005-227257 | 8/2005 |
| JP | 3851395 | 11/2006 |
| WO | 03/008348 | 1/2003 |

OTHER PUBLICATIONS

International Search Report issued Nov. 2, 2010 in International (PCT) Application No. PCT/JP2010/066217.

* cited by examiner

*Primary Examiner* — Sath V Perungavoor
*Assistant Examiner* — Jeffery Williams
(74) *Attorney, Agent, or Firm* — Wenderoth, Lind & Ponack, L.L.P.

(57) ABSTRACT

The problem is solved by generating a gob image A by capturing, with a line scanning camera, an image of a falling gob that has been cut off at an orifice; generating an image B by binarizing the gob image A with a boundary value that turns a general part of the gob black and turns a peripheral lustrous portion and a defect of the gob white; generating an image C by binarizing the gob image A with a boundary value that turns the entire gob white and turns a background black and inverting the black and white; generating an image D by combining the image B and the image C together; setting a region located a given number of pixels inside an outer edge of the black area of the image D as an inspection region; and inspecting the inspection region of the gob image A to determine whether the gob is good.

14 Claims, 9 Drawing Sheets

GOB INSPECTION SYSTEM FOR GLASS PRODUCT

TECHNICAL FIELD

The present invention relates to an inspection system that inspects a gob to be placed in a retold for foreign objects or bubbles and chocks the shape of the gob, in producing a large quantity of glass products, such as glass bottles, in a molding machine.

BACKGROUND ART

Glass products, such as glass bottles, are inspected for defects (e.g., scratches, bubbles, and foreign objects) with visible light after being slowly cooled in a slow-cooling furnace (at a so-called cold end). Typically, as described in Patent Literature (PTL) 1 to PTL 3 listed below, systems used in such inspections illuminate a glass product with a projector while rotating the product, capture the reflected or transmitted light with a camera, and process the resulting image to discover a defect.

PTL 4 to PTL 6 disclose systems and methods for measuring the volume or weight of a gob to be placed in a mold, in producing a large quantity of glass products, such as glass bottles, in a molding machine.

Additionally, PTL 6 describes a technique that involves comparing three-dimensional data of a gob shape with data of a desirable gob shape and adjusting the gob shape to the desirable gob shape to improve the quality of the resulting glass product.

CITATION LIST

Patent Literature

PTL 1: Japanese Unexamined Patent Application Publication No. 2003-4649
PTL 2: Japanese Unexamined Patent Application Publication No. 2000-19130
PTL 3: Japanese Unexamined Patent Application Publication No. 7-103915
PTL 4: Japanese Examined Patent Application Publication No. 63-52326
PTL 5: Japanese Unexamined Patent Application Publication No. 7-33445
PTL 6: International Publication No. WO 2003/8343

SUMMARY OF INVENTION

Technical Problem

In conventional defect inspection for molded glass products, it may be difficult to accurately inspect a product depending on what part of the product is defective. For example, for a glass bottle, it is difficult to discover all defects (e.g., bubbles and foreign objects) in parts with complex shapes, such as the mouth and bottom. This means that some defective products may be erroneously determined to be non-defective and may pass the inspection.

It is therefore desirable to reduce or eliminate such errors in inspection. An object of the present invention is to facilitate detection of foreign objects or bubbles trapped in a gob.

Solution to Problem (Claim 1)
The present invention provides a gob inspection system that includes a line scanning camera configured to scan, in a horizontal direction, a failing gob that has been cut off at an orifice; and
processing means for processing data from the line scanning camera.
The processing means generates a gob image A by arranging lines of the data sequentially in a vertical direction, generates an image B by binarizing the gob image A with a boundary value that turns a general part of the gob black and turns a peripheral lustrous portion and a defect of the gob white,
generates an image C by binarizing the gob image A with a boundary value that turns the entire gob white and turns a background black and inverting the black and white,
generates an image D by combining the image B and the image C together,
sets a region located a given number of pixels inside an enter edge of the black area of the image D as an inspection region, and
inspects the inspection region of the gob image A to determine whether the gob is good.

A gob that has been cut off at the orifice emits light because of a high temperature. The entire gob can be scanned by capturing the gob with the line scanning camera configured to scan a falling gob in the horizontal direction.

The line scanning camera can be placed at any position that allows capturing of a free-falling gob that has been cut off at the orifice. Although there are no specific restrictions, if is preferable that the gob be captured in the horizontal direction.

A typical commercially available line scanning camera that mainly captures visible light can be used as the line scanning camera. It is not particularly necessary to provide a means for illuminating a gob, which itself emits light.

Light emitted from each point inside the gob is reflected and refracted on the outer surface of the gob and travels along a complex light path. Generally, this forms a peripheral lustrous portion which appears brighter than a general part of the gob. The peripheral lustrous portion appears bright even without any defect. Therefore, the inspection region is set, with this peripheral lustrous portion excluded.

If the gob has a defect, such as a bubble or foreign object trapped therein, the corresponding portion generally appears brighter than the other part. Therefore, for example, by detecting, in the inspection region of the gob image A, a point where brightness changes significantly, it is possible to inspect the gob for a defect, such as a bubble or foreign object trapped therein. There are various methods for determining whether the gob is good, and any of these methods can be selected as appropriate.

A commercially available personal computer can be used as the processing means, and is preferably used in combination with a commercially available frame grabber and image processing software.

(Claim 2)
The present invention provides the gob inspection system according to claim 1, wherein if, in the inspection region of the gob image A, the number of pixels with brightness levels higher than a predetermined brightness threshold exceeds a predetermined threshold number of pixels, the processing means determines that the gob is a bad gob.

If the gob has a defect, such as a bubble or foreign object trapped therein, the corresponding portion generally appears brighter than the other part. Therefore, by setting an appropriate brightness level between the brightness of the general part of the gob and the brightness of the defective portion of the gob as a brightness threshold, the number of pixels in the defective portion can be detected.

The threshold number of pixels can be determined by taking into account an acceptable defect level.

(Claim 3)

The present invention provides a gob inspection system that includes a line scanning camera configured to scan, in a horizontal direction, a falling gob that has been cut off at an orifice; and processing means for processing data from the line scanning camera.

The processing means generates a gob image A by arranging lines of the data sequentially in a vertical direction;

generates an image B by binarizing the gob image A with a boundary value that turns a general part of the gob black and turns a peripheral lustrous portion and a defect of the gob white;

generates an image C by binarizing the gob image A with a boundary value that turns the entire gob white and turns a background black and inverting the black and white;

generates an image D by combining the image B and the image C together;

sets a region located a given number of pixels inside an outer edge of the black area of the image D as an inspection region; and performs an inspection on the basis of a white portion in the inspection region of the image D to determine whether the gob is good.

Defects, such as bubbles or foreign objects, appear white in the inspection region of the image D. A gob defect inspection can be carried out by detecting such a white portion.

(Claim 4)

The present invention provides the gob inspection system according to Claim 3, wherein if the total number of pixels in the white portion in the inspection region of the image D exceeds a predetermined threshold number of pixels, the processing means determines that the gob is a bad gob.

In addition to this typical method of determination, there is a method in which if there are more than one white portions and number of pixels of one of the white portions exceeds a predetermined number of pixels, the gob is determined to be a bad gob. Any method of such determination can be selected as appropriate.

(Claim 5)

The present invention provides a gob inspection system that includes a line scanning camera configured to scan, in a horizontal direction, a falling gob that has been cut off at an orifice; and processing means for processing data from the line scanning camera.

The processing means generates a gob image A by arranging lines of the data sequentially in a vertical direction;

generates an image B by binarizing the gob image A with a boundary value that turns a general part of the gob black and turns a peripheral lustrous portion and a defect of the gob white;

generates an image C by binarizing the gob image A with a boundary value that turns the entire gob white and turns a background black and inverting the black and white;

generates an image E by eroding an edge of a white area in the image B by a width of a predetermined number of pixels;

generates an image F by dilating an edge of a white area in the image E by a width of a predetermined number of pixels;

generates an image G by combining the image F and the image C together; and performs an inspection on the basis of a white portion in the black area of the image G to determine whether the gob is good.

This inspection system can perform an inspection for defects, such as bubbles and foreign objects, without setting an inspection region. When an inspection region is set, a defect located near the peripheral lustrous portion may be excluded from the inspection region. With, this inspection system, the occurrence of such a problem can be avoided.

Defects, such as bubbles or foreign objects, appear white in the black area of the image G. A gob defect inspection can be carried out by detecting such a white portion.

(Claim 6)

The present invention provides the gob inspection, system according to Claim 5, wherein if the total number of pixels in the white portion in the black area of the image G exceeds a predetermined threshold number of pixels, the processing means determines that the gob is a bad gob.

In addition to this typical method of determination, there is a method in which if there are more than one white portions and number of pixels of one of the white portions exceeds a predetermined number of pixels, the gob is determined to be a bad gob. Any method of such determination can be selected as appropriate.

(Claim 7)

The present invention provides the gob inspection system that includes a line scanning camera configured to scan, in a horizontal direction, a falling gob that has been cut off at an orifice; and processing means for processing data from the line scanning camera.

The processing means generates a gob image A by arranging lines of the data sequentially in a vertical direction;

generates an image H by binarizing the gob image A with a boundary value that turns the entire gob white and turns a background black;

generates an image I by trimming off a protrusion of the white area of the image H;

generates an image J by subtracting the image I from the image H; and determines that the gob is a bad gob if the total number of pixels in a white portion in the black area of the image J exceeds a predetermined threshold number of pixels.

This inspection system can detect a protruding foreign object protruding from a gob. None of the other inspection systems described above can detect such a protruding foreign object. This is because such a protruding foreign object is excluded as a peripheral lustrous portion.

A protruding foreign object portion is white in the image J. In the image I obtained by trimming off the protrusion of the white area in the image H, some part other than the protruding foreign object may have been slightly trimmed off. However, by appropriately setting a threshold number of pixels, only the protruding foreign object can be detected.

The inspection system of the present invention can use a combination of more than one, or all, of the following methods: a method in which the inspection system of any one of Claims 1 to 4 inspects the inspection region, a method in which the inspection system of Claim 5 or 6 inspects the image G, and a method in which the inspection system of Claim 7 inspects the image J. When a gob is inspected using all methods combined, and is determined to be defective by at least one of the methods used, the gob is determined to be a bad gob.

(Claim 8)

The present invention provides the gob inspection system according to any one of Claims 1 to 7, wherein the gob inspection system includes a plurality of line scanning cameras, inspects each of gob images from the respective line scanning cameras, and determines that the gob is a bad gob if, on the basis of at least one of the gob images, the gob is determined to be a bad gob.

FIG. 3 is a diagram of a gob as viewed from above. As illustrated, light from inside a gob 5 is refracted on the outer surface of the gob and reaches a camera 4. Diagonally shaded areas in FIG. 3 represent invisible portions 58 that cannot be seen from the camera 4. The entire gob cannot be fully inspected with only one camera. It is thus necessary that a plurality of cameras be placed at different angles.

A gob determined to be defective by the inspection system of the present invention may be removed by a gob removing device before being fed into a mold, or may be removed by a rejector at a hot end (i.e., before entering a slow-cooling furnace) after being molded into a product.

Advantageous Effects of Invention

Since the shapes of gobs are simpler than those of products, trapped bubbles and foreign objects can be detected with high accuracy.

By removing a product molded from a bad gob at a hot end, it is possible to significantly reduce the risk that a defective product will pass the inspection at a cold end.

Using a line scanning camera can facilitate data analysis at a low facility cost. It is thus possible to fully inspect ail gobs that have been cut off at about two-second intervals.

DESCRIPTION OF EMBODIMENTS

A description will now be given of an embodiment which is applied to a gob inspection in the process of molding glass products (glass bottles) in a so-called IS molding machine.

Figure 1:
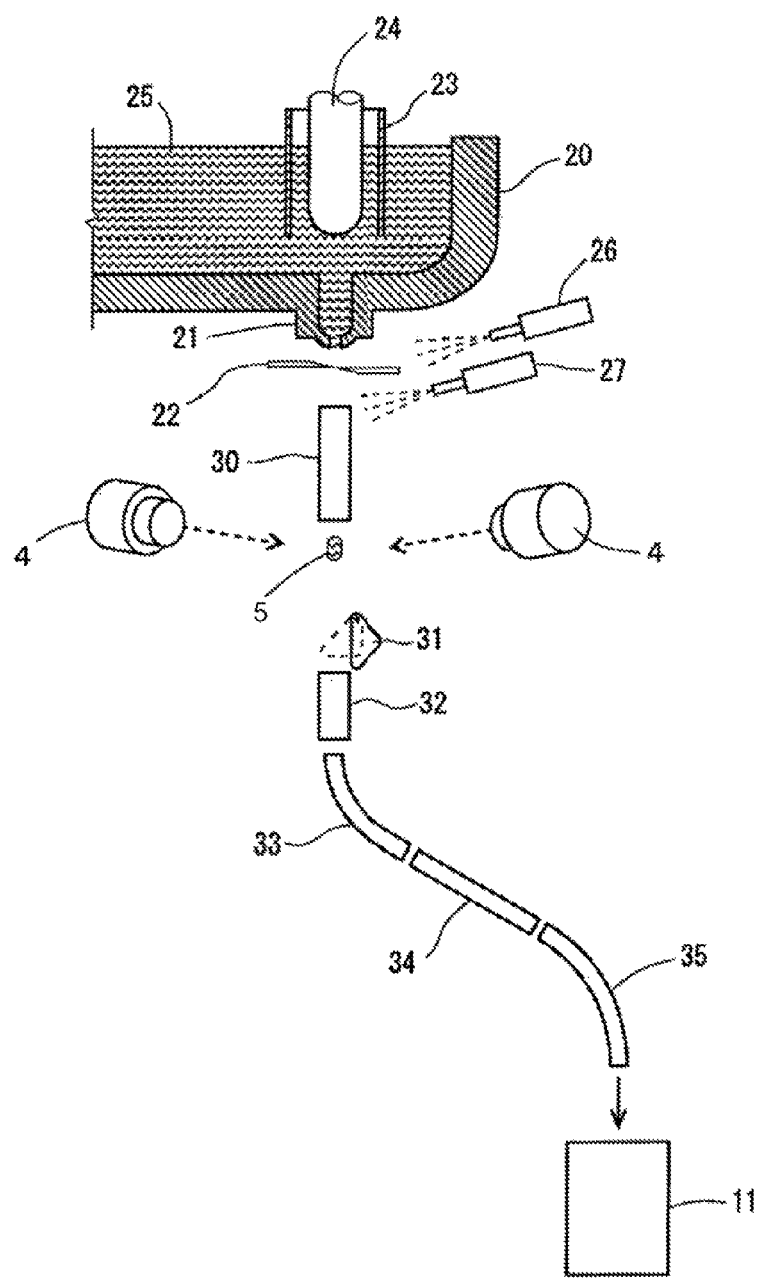
FIG. 1 is a diagram illustrating a process in which a gob is cut off and fed into a mold.

FIG. 1 illustrates a falling gob 5 that has been cut off at an orifice 21.

A spout 20 filled with molten glass 25 is provided with a rotating tube 23 and a plunger 24 that moves up and down. When the plunger 24 is lowered to squeeze the molten glass 25 out of the orifice 21, shears 22 are activated to cut the molten glass 25. The gob 5 cut off by the shears 22 falls. The falling gob 5 passes through a gob distributing means, including an upper funnel 30, a lower funnel 32, a scoop 33, a trough 34, and a deflector 35, and is fed into a mold 11 (blank mold). Each of multiple sections of the molding machine is provided with the trough 34, the deflector 35, and the mold 11. The scoop 33 sequentially feeds gobs into respective molds in the multiple sections while changing its orientation.

In FIG. 1, reference numeral 26 denotes a shear spray unit that sprays water to cool the shears 22, and reference numeral 27 denotes a cooling spray unit that sprays water to cool the upper funnel 30.

A plurality of line scanning cameras 4 are installed to capture the image of the falling gob 5 that leaves the upper funnel 30 and enters the lower funnel 32. The line scanning cameras, which are installed in a high-temperature environment, are preferably each placed in a cooling box (not shown) and cooled. Data from the line scanning cameras 4 is transmitted through a frame grabber to a personal computer, which performs image processing to determine whether bubbles or foreign objects are trapped in the gob.

The line scanning cameras 4 capture the surface of a moving body with a horizontal linear field of view, scans the moving body at predetermined intervals, and outputs the captured image as a video signal. The cameras used here have 2048 pixels in the horizontal direction and are capable of capturing an image with high resolution. As a gob moves in a direction perpendicular to the rows of pixels, the entire image of the gob is captured as image data.

A processing means is a commercially available computer (personal computer) that includes a storage means (memory and hard disk) and is connected to a display means (monitor) and an input means (keyboard and mouse). Desired information, such as a gob image and various images obtained by processing the gob image, can be displayed on the display means. The processing means includes commercially available image processing software and is connected to a frame grabber.

Figure 2:
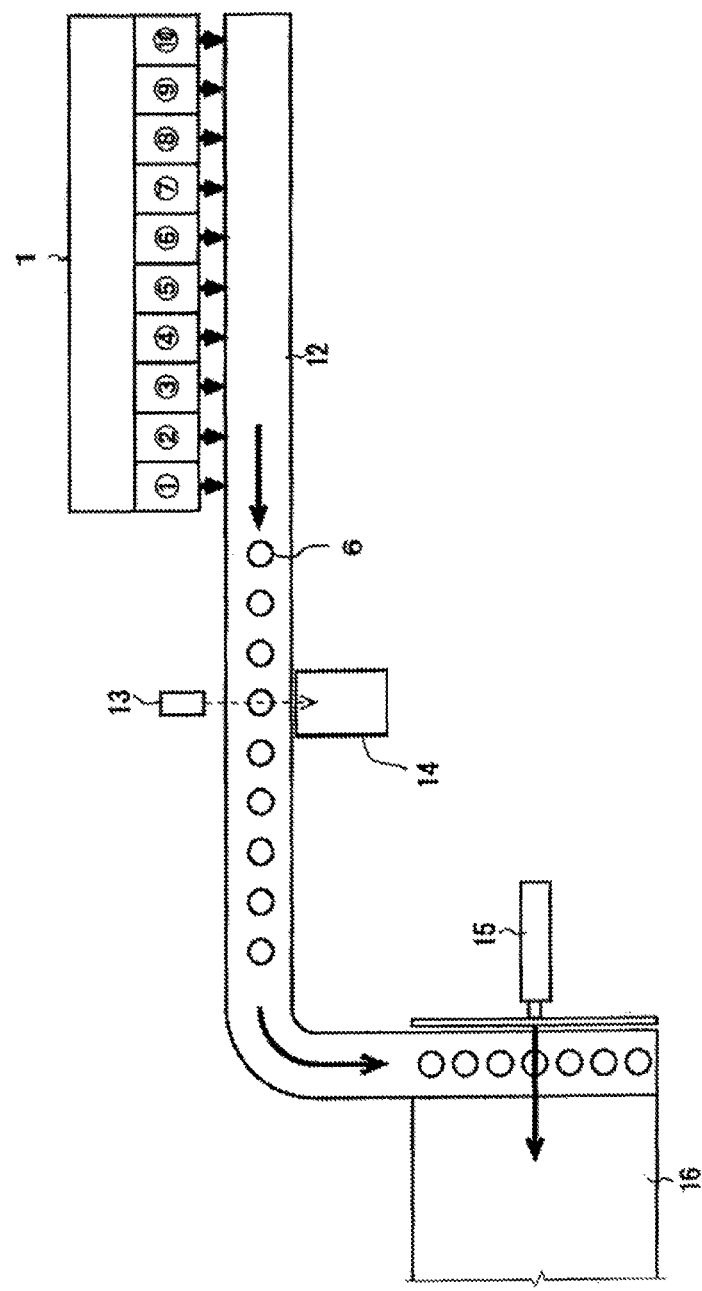
FIG. 2 illustrates a process in which glass products molded by a molding machine are conveyed into a slow-cooling furnace.
Figure 3:
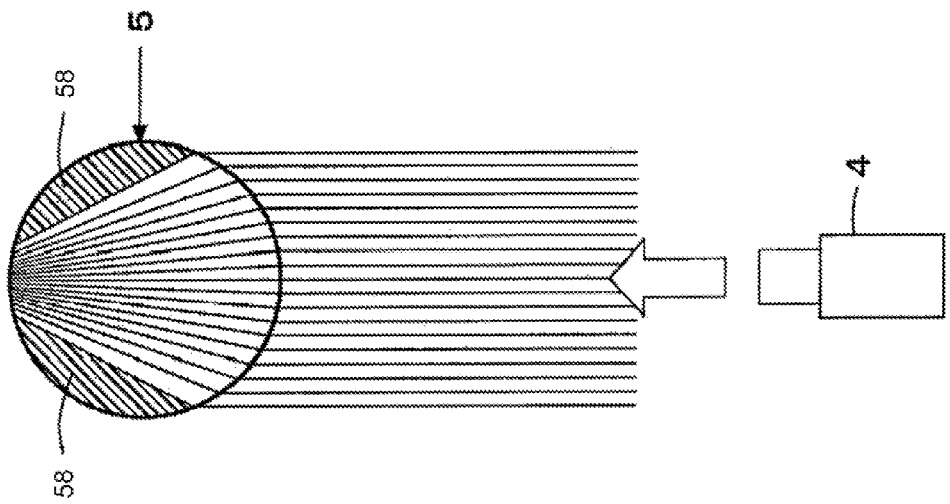
FIG. 3 is a diagram of a gob as viewed from above, and illustrates, parts of the gob invisible from a camera.

As illustrated in FIG. 2, the IS molding machine 1 has 10 sections, from a first section to a tenth section. Circled numbers in FIG. 2 represent section numbers. The first section is located on the most downstream side of a conveyor 12, and the tenth section is located on the most upstream side of the conveyor 12.

A control system attached to the IS molding machine 1 provides a shear cut signal, a timing signal, and a reset signal.

A shear cut signal is a pulse signal provided by the control system to activate the shears 22.

A timing signal is a pulse signal synchronized with the speed of operation of the IS molding machine. For example, 1800 pulses are output in one cycle of operation (i.e., until completion of one molding operation in all the sections).

The shear cut timing of cutting off a gob, the action of every part of the molding machine, and the conveyance speed of the conveyor 12 are all synchronized with the timing signal.

One pulse of a reset signal is output every time the IS molding machine 1 completes one cycle of operation.

By receiving a shear cut signal, a timing signal, and a reset signal from the control system of the IS molding machine 1, the processing means can recognize the timing of when the glass product 6 molded from an inspected gob is conveyed to the front of a rejector 13 and when the rejector 13 is to foe activated.

FIG. 2 illustrates a process in which glass products 6 (glass bottles) molded by the molding machine 1 are conveyed into a slow-cooling furnace 16.

Gobs inspected by the inspection, system, of the present invention are placed in the blank molds of the IS molding machine 1, where parison molding and finish molding are performed. The resulting glass products 6 are conveyed on the conveyor 12 toward the slow-cooling furnace 16 and pushed into the slow-cooling furnace 16 by a pusher 15.

The rejector 13 is disposed beside the conveyor 12 and located between the IS molding machine 1 and the slow-cooling furnace 16.

The processing means activates the rejector 13 when the glass product 6 molded from a gob 5 which has been determined to be defective is conveyed to the front of the rejector 13. The rejector 13 blows this glass product toward a disposal unit 14 to remove it from the conveyer 12.

Data (line data) from the line scanning cameras 4 is transmitted to the processing means and analyzed. The processing means first generates a gob image A by arranging lines of data from the line scanning cameras 4 sequentially in a vertical direction.

(Setting of Inspection Region)

Figure 4:
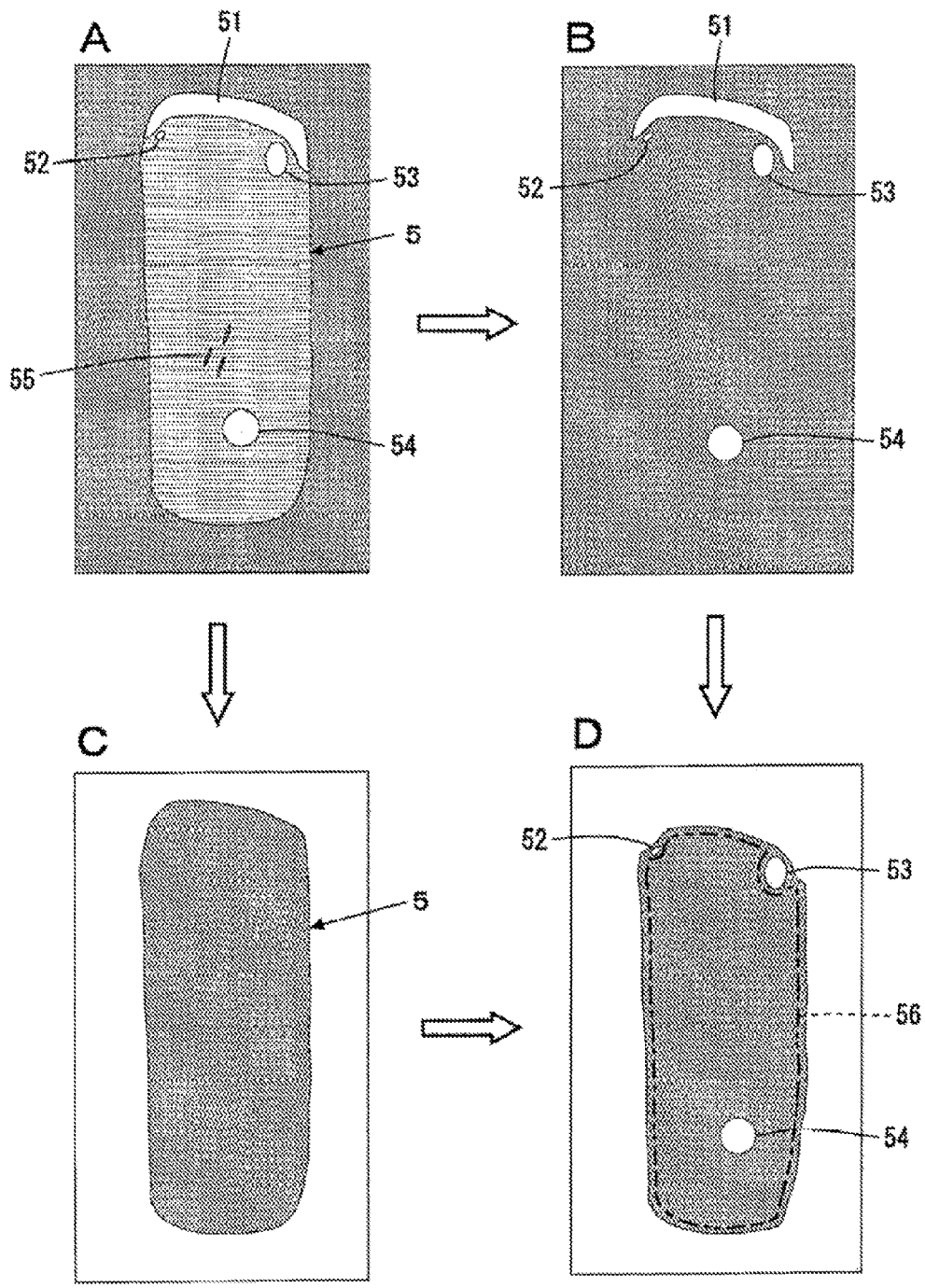
FIG. 4 illustrates how an inspection region is generated.

As illustrated in FIG. 4, a processing means generates an image B and an image C from the gob image A, generates an image D by combining the image B and the image C together, and sets an inspection region from the image D.

Figure 5:
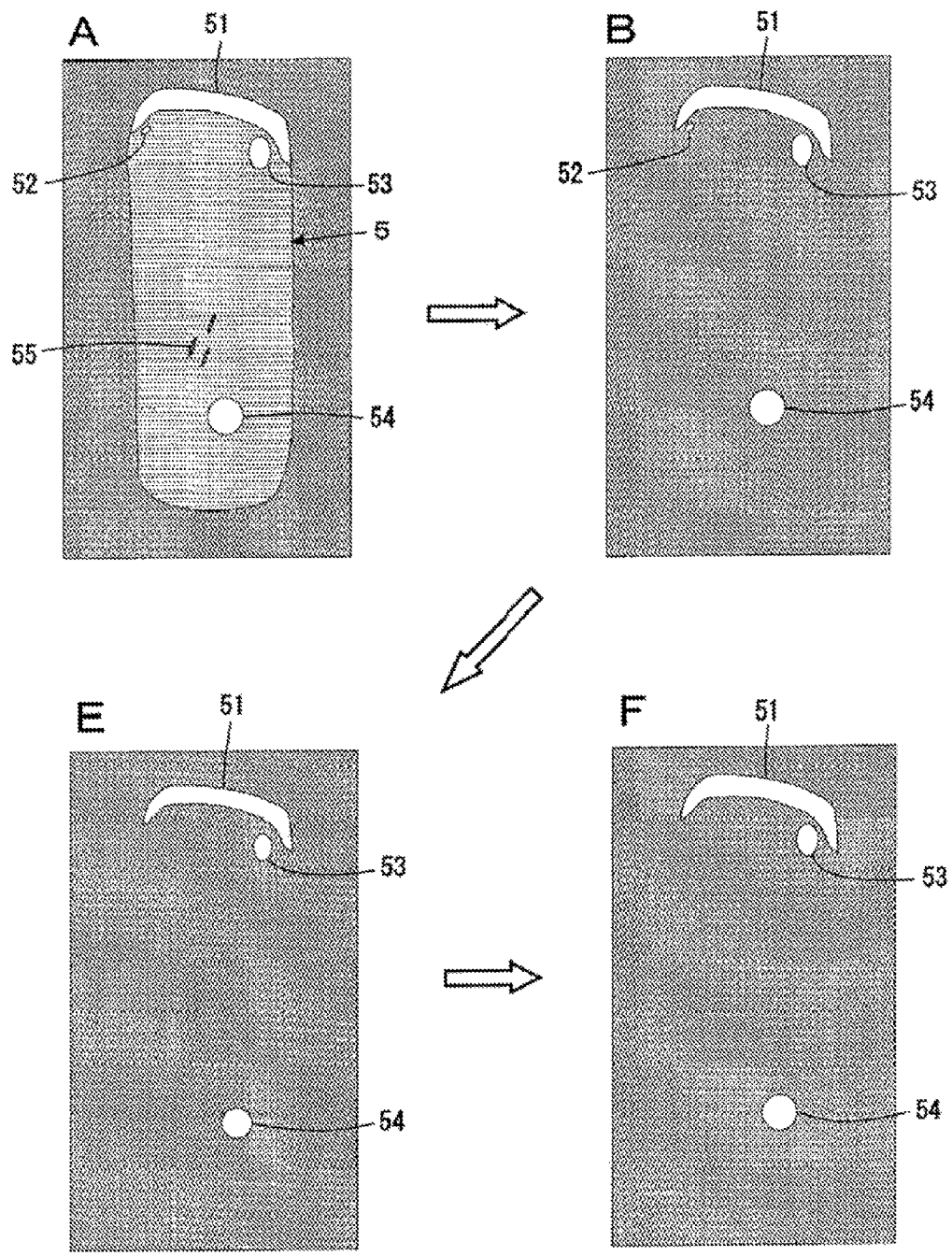
FIG. 5 illustrates a process of generating an image F from a gob image A.

In the gob image A illustrated in FIG. 4 and FIG. 5, reference numeral 51 denotes a peripheral lustrous portion, which is not a defect. The peripheral lustrous portion 51 appears bright, because light from inside the gob refracts and reflects on the outer surface of the gob. Reference numeral 52 denotes a so-called island, which is not a defect. The island 52 is a small portion that also appears bright, because the peripheral lustrous portion 51 is located in the vicinity thereof. The island 52 may be produced depending on the shape of the gob. Reference numeral 53 denotes a defect, such as a bubble or foreign object, which is located near the peripheral lustrous portion 51 and appears bright. Reference numeral 54 denotes a defect, such as a bubble or foreign object, which is located far from the peripheral lustrous portion 51 and appears bright. Reference numeral 55 denotes small water droplets sprayed from the shear spray unit 26 or the cooling spray unit 27. The image of the water droplets 55 is captured together with that of the gob by the cameras 4 in an overlapping manner. The water droplets 55 appear dark.

The image B is obtained by binarizing the gob image A. An appropriate brightness level between, the brightness of the peripheral lustrous portion 51, island 52, and defects 53 and 54 and the brightness of a general part of the gob is selected as a boundary value for the binarization. In the image B, the peripheral lustrous portion 51, the island 52, and the defects 53 and 54 are white, and the other part is black.

The image C is obtained by binarizing the gob image A and inverting the black and white. An appropriate brightness level higher than the brightness of the background is selected as a boundary value for the binarization so that the entire gob turns white. In the image C, the entire gob is black and the background is white.

The image D is obtained by combining the image B and the image C together. The following rules are used to combine the images: black+black=black, black+white=white, and white+white=white. In the image D, the outer shape of the black area is obtained by subtracting the peripheral lustrous portion 51 from the outer shape of the gob. The island 52 and the defects 53 and 54 turn white and appear in the black area.

As indicated by a broken line in the image D in FIG. 4, a region located a given number of pixels inside the cater edge of the black area in the image D is set as an inspection region 56. This number of pixels is slightly larger than that between the peripheral lustrous portion 51 and the island 52. Specifically, this number of pixels is about 5 to 20, and is preferably about 10 in most cases. Thus, as shown in the upper left of the image D, the island 52 (which is not a defect) is excluded from the inspection region 56, so that the island 52 is prevented from being determined to be a defect. However, as shown in the upper right of the image D, if the defect 53 is located near the peripheral lustrous portion 51, the defect 53 is also excluded from the inspection region 56. Such a defect as the defect 53 is inspected by a method described below.

(Inspection of Inspection Region)

The inspection region can be inspected in various ways.

For example, assume that the inspection region is extracted from the gob image A. Then if, in the extracted, data, the number of points where the brightness changes significantly (i.e., where a difference in brightness between adjacent pixels is larger than a predetermined brightness threshold) is larger than a predetermined threshold value, the gob can be determined to be a bad gob.

Also assume that the inspection region is extracted from the gob image A. Then if, in the extracted data, the number of pixels with brightness levels higher than a predetermined brightness threshold exceeds a predetermined threshold number of pixels, the gob can be determined to be a bad gob.

In the inspection region 56 of the image D, if the total number of pixels in one or more white portions exceeds a predetermined threshold number of pixels, the gob can be determined to be a bad gob.

Also, in the inspection region 56 of the image D, if there are more than one white portions and the number of pixels in one of the white portions exceeds a predetermined threshold number of pixels, the gob can be determined to be a bad gob.

(Inspection without Inspection Region)

Figure 6:
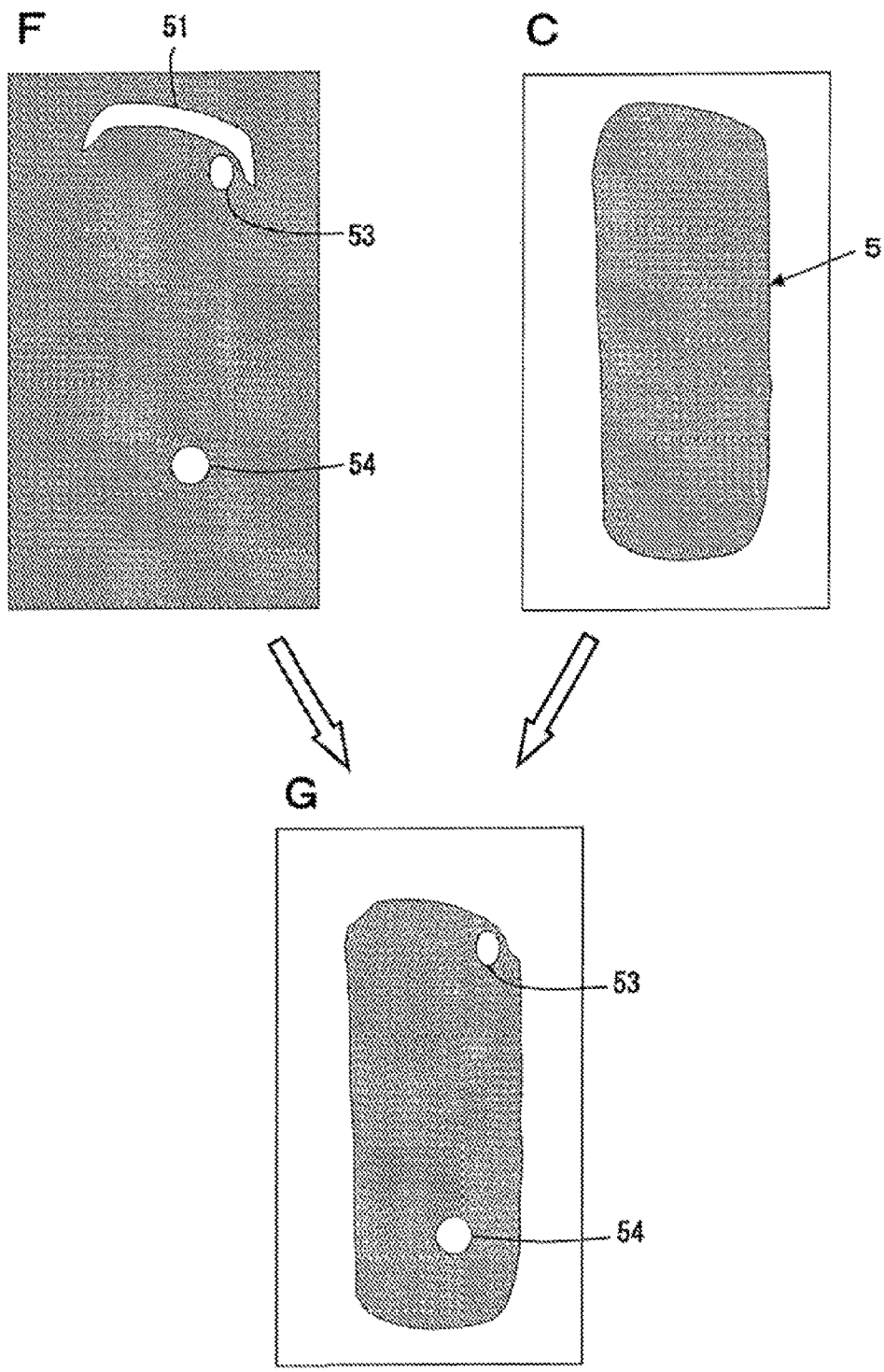
FIG. 6 illustrates a process of generating an image G from the image F.

As illustrated in FIG. 5, the processing means generates the image B by binarizing the gob image A, generates an image E from the image B, and generates an image F from the image E. Also, as illustrated in FIG. 6, the control means generates an image G by combining the image F and the image C obtained by binarizing the gob image A and inverting the black and white, and inspects the gob on the basis of the image G.

The image B, which is obtained by binarizing the gob image A, and the image C, which is obtained by binarizing the gob image A and inverting the black and white, are the same as those described in the embodiment above. The image E is obtained by eroding the edge of each white area in the image B by a width of a predetermined number of pixels (e.g., 20 pixels). This erosion is a function normally included in typical image processing software installed in a personal computer. In the image E, the island 52 disappears and the peripheral lustrous portion 51 and the defects 53 and 54 shrink, as a result of the erosion. The island disappears after this operation, because it is smaller in size than the defects. The image F is obtained by dilating the edge of each white area in the image E by a width of a predetermined number of pixels (e.g., 20 pixels). This dilatation is also a function normally included in typical image processing software installed in a personal computer. A comparison between the image F and the image B shows that although the island 52 disappears in the image F, the peripheral lustrous portion 51 and the defects 53 and 54 in the image F are substantially the same in shape and size as those in the image B. Since the island (which is not a defect) disappears, the island is prevented from being erroneously determined to be a defect.

The image G is obtained by combining the image C and the image F together. In the black area of the image G, only the defects 53 and 54 remain and the peripheral lustrous portion 51 and the island 52 disappear. Therefore, whether the gob is good or bad can be determined by inspecting white portions in the black area of the image G.

The black area of the image G can be inspected in various ways.

For example, in the black area of the image G, if the total number of pixels in one or more white portions exceeds a predetermined threshold number of pixels, the gob can be determined to be a bad gob.

Also, in the black area of the image G, if there are more than one white portions and the number of pixels in one of the white portions exceeds a predetermined threshold number of pixels, the gob can foe determined to be a bad gob.

(Inspection of Protruding Foreign Object)

Figure 7:
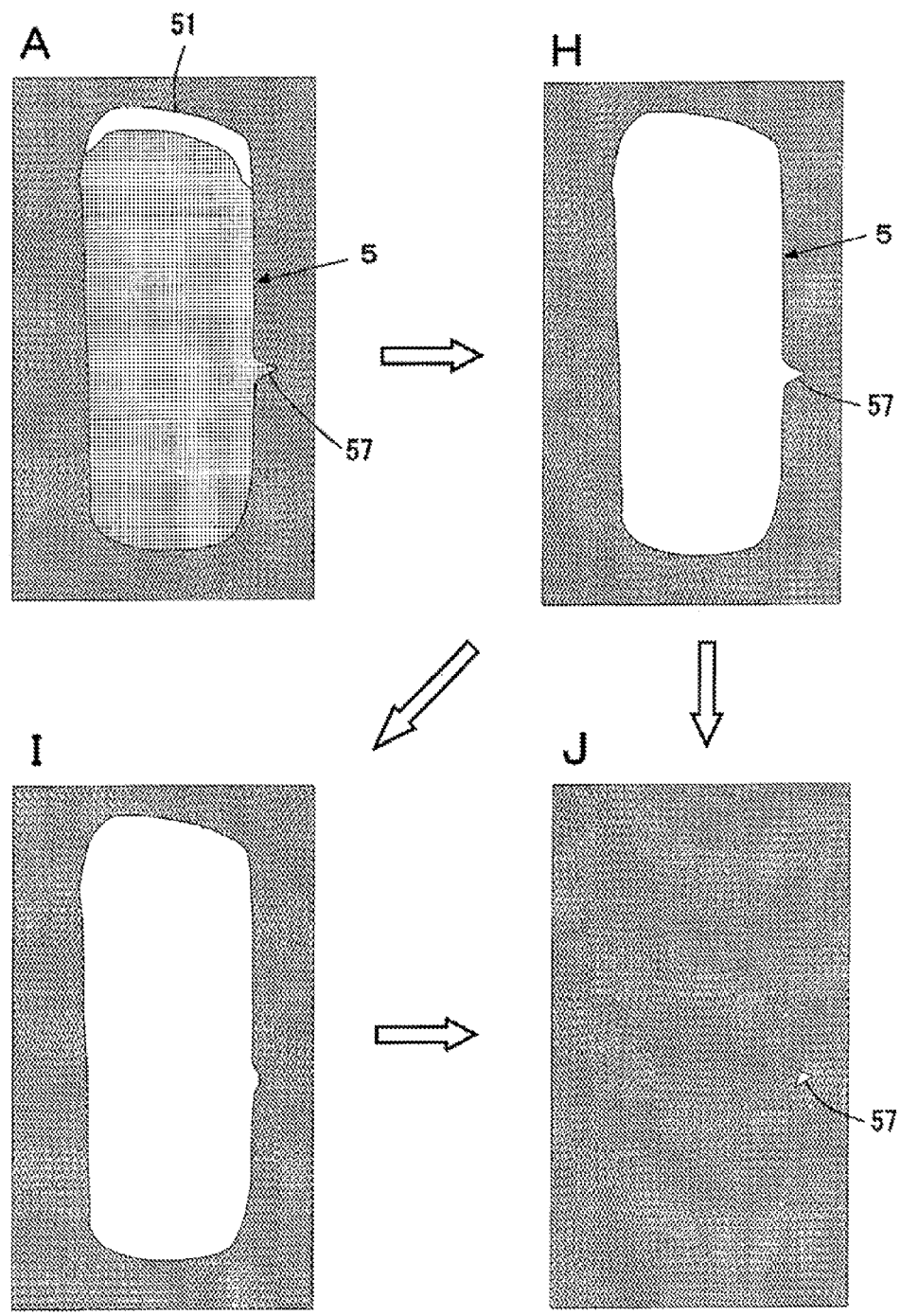
FIG. 7 illustrates a process of generating an image J from the gob image A.

As illustrated in FIG. 7, the processing means generates an image H by binarizing the gob image A, generates an image I from the image H, and generates an image J by subtracting the image I from the image H. If the total number of pixels in a white portion in the black area of the image J exceeds a predetermined threshold number of pixels, the control means determines that the gob is a bad gob.

The image H is obtained by binarizing the gob image A. An appropriate brightness level higher than the brightness of the background is selected as a boundary value for the binarization so that the entire gob turns white. In the image H, the entire gob is white and the background is black. The image I is obtained by trimming off a protrusion 57 of the white area in the image H. This trimming is a function normally included in typical image processing software installed in a personal computer.

The image J is obtained by subtracting the image I from the image H. The following rules are used in image subtraction: black−black=black, black−white=black, white−black=white, and white−white=black.

Only the protrusion 57 is white in the image J. In the image I obtained by trimming off the protrusion of the white area in the image B, some part other than the protruding foreign object may have been slightly trimmed off. In this case, a white portion (which is not a defect) other than the protruding foreign object slightly appears in the image J. However, by appropriately selecting a threshold number of pixels (e.g., five pixels), the white portion other than the protruding foreign object can be prevented from being determined to be a defect.

Figure 8:
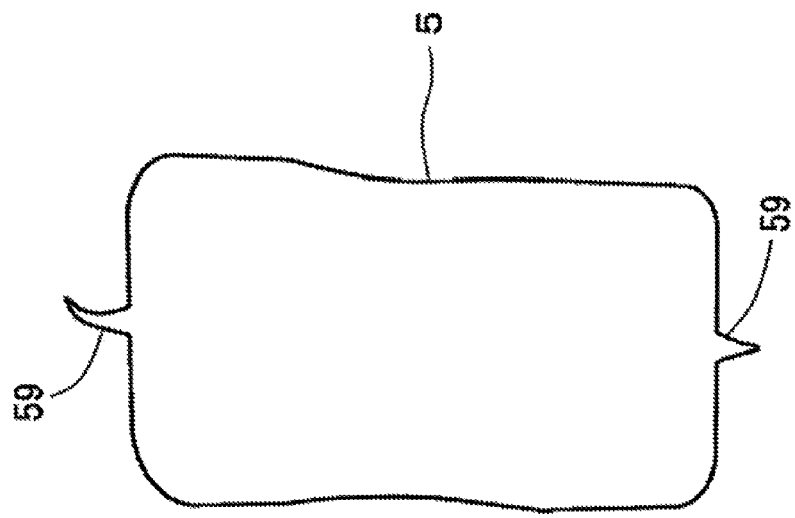
FIG. 8 illustrates a gob with stringy portions, which are defects.
Figure 9:
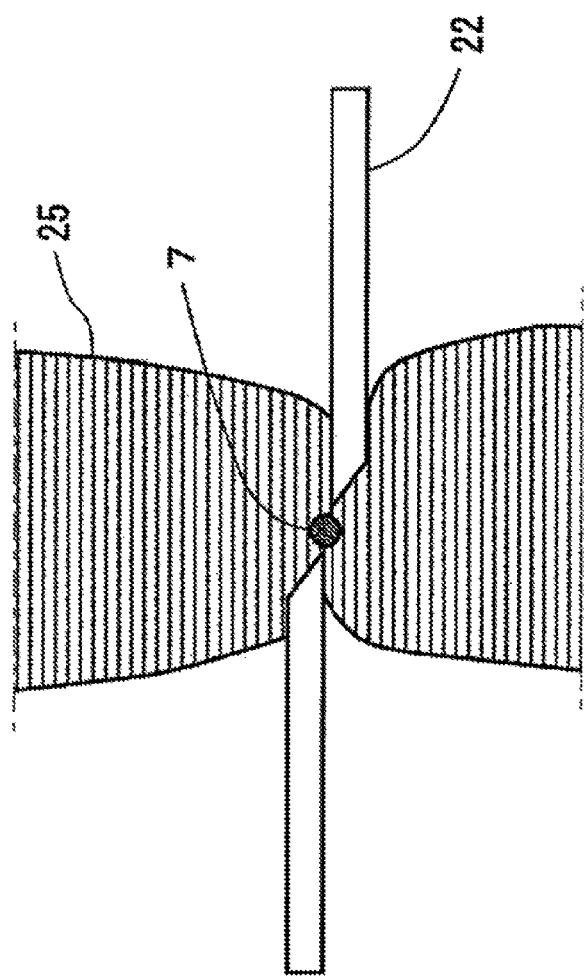
FIG. 9 illustrates how stringiness occurs.

The system that detects such a protruding foreign object can also detect a gob defect called "stringiness". FIG. 8 illustrates a gob with stringy portions 59, which are narrow string-like protruding defects. The stringy portions 59 remain as streaks on the surface of the molded glass product. This results in noticeable visual defects. The stringy portions 59 are formed when, as illustrated in FIG. 9, there is a hard foreign object 7 at a point where the molten glass 25 is cut by the shears 22. The presence of the hard foreign object may affect the cutting action of the shears, so that gobs subsequently cut off by the shears may be determined to be bad gobs.

If a gob is determined to be a bad gob on the basis of the image J, the processing means can activate an alarm (e.g., beeper or flashing light). When the alarm is activated, the operator immediately checks the condition of the shear blades, and replaces the shears if necessary. This can prevent a series of occurrences of a bad gob.

When the processing means determines that an image-processed gob is a bad gob that has bubbles or foreign objects trapped therein, the processing means can activate a gob removing device 31 (FIG. 1) to remove the gob.

Alternatively, instead of removing a bad gob, a glass product molded from the bad gob may be removed by the rejector while the glass product is being conveyed on the conveyor from the molding machine to the slow-cooling furnace. This is because if the gob is removed, the corresponding mold where no product is formed in one cycle is cooled down, which may cause micro-cracks or wrinkles in a product to be subsequently molded in this mold. A product molded from a bad gob is removed in the passage from the molding machine to the slow-cooling furnace, because by transmitting a timing signal of the molding machine to the processing means, the processing means can recognize the timing of when each product molded from an inspected gob reaches the front of the rejector and is to be removed. Thus, a product molded from a bad gob can be accurately removed. A known rejector can be used here. For example, the rejector may be one that blows a glass product off the conveyor with air, or one that pushes the glass product out of the conveyor.

REFERENCE SIGNS LIST

1: molding machine
11: mold
12: conveyor
13: rejector
14: disposal unit
15: pusher
16: slow-cooling furnace
20: spout
21: orifice
22: shears
23: tube
24: plunger
25: molten glass
26: shear spray unit
27: cooling spray unit
30: upper funnel
31: gob removing device
32: lower funnel
33: scoop
34: trough
35: deflector
4: camera
5: gob
51: peripheral lustrous portion
52: island
53: defect
54: defect
55: water droplet
56: inspection region
57: protrusion
56: invisible portion
59: stringy portion
6: glass product
7: foreign object
A: gob image
B: image B
C: image C
D: image D
B: image E
F: image F
G: image G
H: image H
I: image I
J: image J

The invention claimed is:

1. A gob inspection system comprising:
   a line scanning camera configured to scan, in a horizontal direction, a falling gob that has been cut off at an orifice; and
   processing means for processing data from the line scanning camera, wherein the processing means generates a gob image A by arranging lines of the data sequentially in a vertical direction;

generates an image B by binarizing the gob image A with a boundary value that turns a general part of the gob black and turns a peripheral lustrous portion and a defect of the gob white;

generates an image C by binarizing the gob image A with a boundary value that turns the entire gob white and turns a background black and inverting the black and white;

generates an image D by combining the image B and the image C together;

sets a region located a given number of pixels inside an outer edge of the black area of the image D as an inspection region; and inspects the inspection region of the gob image A to determine whether the gob is good.

2. The gob inspection system according to claim 1, wherein if, in the inspection region of the gob image A, the number of pixels with brightness levels higher than a predetermined brightness threshold exceeds a predetermined threshold number of pixels, the processing means determines that the gob is a bad gob.

3. A gob inspection system comprising:

a line scanning camera configured to scan, in a horizontal direction, a falling gob that has been cut off at an orifice; and processing means for processing data from the line scanning camera, wherein the processing means generates a gob image A by arranging lines of the data sequentially in a vertical direction;

generates an image B by binarizing the gob image A with a boundary value that turns a general part of the gob black and turns a peripheral lustrous portion and a defect of the gob white;

generates an image C by binarizing the gob image A with a boundary value that turns the entire gob white and turns a background black and inverting the black and white;

generates an image D by combining the image B and the image C together;

sets a region located a given number of pixels inside an outer edge of the black area of the image D as an inspection region; and performs an inspection on the basis of a white portion in the inspection region of the image D to determine whether the gob is good.

4. The gob inspection system according to claim 3, wherein if the total number of pixels in the white portion in the inspection region of the image D exceeds a predetermined threshold number of pixels, the processing means determines that the gob is a bad gob.

5. A gob inspection system comprising:

a line scanning camera configured to scan, in a horizontal direction, a falling gob that has been cut off at an orifice; and processing means for processing data from the line scanning camera, wherein the processing means generates a gob image A by arranging lines of the data sequentially in a vertical direction;

generates an image B by binarizing the gob image A with a boundary value that turns a general part of the gob black and turns a peripheral lustrous portion and a defect of the gob white;

generates an image C by binarizing the gob image A with a boundary value that turns the entire gob white and turns a background black and inverting the black and white;

generates an image E by eroding an edge of a white area in the image B by a width of a predetermined number of pixels;

generates an image F by dilating an edge of a white area in the image E by a width of a predetermined number of pixels;

generates an image G by combining the image F and the image C together; and performs an inspection on the basis of a white portion in the black area of the image G to determine whether the gob is good.

6. The gob inspection system according to claim 5, wherein if the total number of pixels in the white portion in the black area of the image G exceeds a predetermined threshold number of pixels, the processing means determines that the gob is a bad gob.

7. The gob inspection system, comprising:

a line scanning camera configured to scan, in a horizontal direction, a falling gob that has been cut off at an orifice; and processing means for processing data from the line scanning camera, wherein the processing means generates a gob image A by arranging lines of the data sequentially in a vertical direction;

generates an image H by binarizing the gob image A with a boundary value that turns the entire gob white and turns a background black;

generates an image I by trimming off a protrusion of the white area of the image H;

generates an image J by subtracting the image I from the image H; and determines that the gob is a bad gob if the total number of pixels in a white portion in the black area of the image J exceeds a predetermined threshold number of pixels.

8. The gob inspection system according to claim 1, wherein the gob inspection system includes a plurality of line scanning cameras, inspects each of gob images from the respective line scanning cameras, and determines that the gob is a bad gob if, on the basis of at least one of the gob images, the gob is determined to be a bad gob.

9. The gob inspection system according to claim 2, wherein the gob inspection system includes a plurality of line scanning cameras, inspects each of gob images from the respective line scanning cameras, and determines that the gob is a bad gob if, on the basis of at least one of the gob images, the gob is determined to be a bad gob.

10. The gob inspection system according to claim 3, wherein the gob inspection system includes a plurality of line scanning cameras, inspects each of gob images from the respective line scanning cameras, and determines that the gob is a bad gob if, on the basis of at least one of the gob images, the gob is determined to be a bad gob.

11. The gob inspection system according to claim 4, wherein the gob inspection system includes a plurality of line scanning cameras, inspects each of gob images from the respective line scanning cameras, and determines that the gob is a bad gob if, on the basis of at least one of the gob images, the gob is determined to be a bad gob.

12. The gob inspection system according to claim 5, wherein the gob inspection system includes a plurality of line scanning cameras, inspects each of gob images from the respective line scanning cameras, and determines that the gob is a bad gob if, on the basis of at least one of the gob images, the gob is determined to be a bad gob.

13. The gob inspection system according to claim 6, wherein the gob inspection system includes a plurality of line scanning cameras, inspects each of gob images from the respective line scanning cameras, and determines that the gob is a bad gob if, on the basis of at least one of the gob images, the gob is determined to be a bad gob.

14. The gob inspection system according to claim 7, wherein the gob inspection system includes a plurality of line scanning cameras, inspects each of gob images from the respective line scanning cameras, and determines that the gob is a bad gob if, on the basis of at least one of the gob images, the gob is determined to be a bad gob.

* * * * *